(12) United States Patent
Meeks et al.

(10) Patent No.: US 7,161,668 B2
(45) Date of Patent: *Jan. 9, 2007

(54) WAFER EDGE INSPECTION

(75) Inventors: Steven W. Meeks, Fremont, CA (US); Rusmin Kudinar, Fremont, CA (US); William R. Wheeler, Saratoga, CA (US); Hung Phi Nguyen, Santa Clara, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/196,540

(22) Filed: Aug. 3, 2005

(65) Prior Publication Data

US 2006/0250610 A1 Nov. 9, 2006

Related U.S. Application Data

(63) Continuation-in-part of application No. 11/123,913, filed on May 6, 2005.

(51) Int. Cl.
G01N 21/88 (2006.01)

(52) U.S. Cl. .................................................. 356/237.2

(58) Field of Classification Search .. 356/237.2–238.5, 356/445–448
See application file for complete search history.

(56) References Cited

U.S. PATENT DOCUMENTS

| | | | | |
|---|---|---|---|---|
| 2,593,189 A | * | 4/1952 | Rinia et al. | .................. 396/351 |
| 4,226,501 A | * | 10/1980 | Shafer | ........................ 359/366 |
| 4,585,348 A | | 4/1986 | Chastang | |
| 4,870,631 A | | 9/1989 | Stoddard | |
| 4,873,430 A | | 10/1989 | Juliana | |
| 5,048,970 A | * | 9/1991 | Milosevic et al. | .......... 356/445 |
| 5,106,196 A | * | 4/1992 | Brierley | ....................... 356/445 |
| 5,125,741 A | * | 6/1992 | Okada et al. | ............. 356/237.2 |
| 5,189,481 A | | 2/1993 | Jann | |
| 5,270,794 A | | 12/1993 | Tsuji | |
| 5,392,116 A | | 2/1995 | Makosh | |
| 5,416,594 A | | 5/1995 | Gross | |
| 5,610,897 A | | 3/1997 | Yamamoto | |
| 5,633,747 A | | 5/1997 | Nikoonahad | |
| 5,644,562 A | | 7/1997 | de Groot | |
| 5,864,394 A | | 1/1999 | Jordan | |
| 5,880,838 A | | 3/1999 | Marx | |
| 5,903,342 A | | 5/1999 | Yatsugake | |
| 5,986,763 A | | 11/1999 | Inoue | |
| 5,995,226 A | | 11/1999 | Abe | |
| 6,031,615 A | | 2/2000 | Meeks | |
| 6,081,325 A | | 6/2000 | Leslie | |
| 6,130,749 A | | 10/2000 | Meeks | |
| 6,198,533 B1 | | 3/2001 | Meeks | |
| 6,229,610 B1 | | 5/2001 | Meeks | |
| 6,268,919 B1 | | 7/2001 | Meeks | |
| 6,392,749 B1 | | 5/2002 | Meeks | |
| 6,624,884 B1 | | 9/2003 | Imaino | |
| 6,665,078 B1 | | 12/2003 | Meeks | |
| 6,687,008 B1 | | 2/2004 | Peale | |
| 6,704,435 B1 | | 3/2004 | Imaino | |
| 6,717,671 B1 | | 4/2004 | Meeks | |
| 6,751,044 B1 | | 6/2004 | Meeks | |

(Continued)

*Primary Examiner*—Richard A. Rosenberger
(74) *Attorney, Agent, or Firm*—Caven & Aghevli LLC

(57) ABSTRACT

In one embodiment, a surface analyzer system comprises a radiation targeting assembly to target a radiation beam onto a surface; and a reflected radiation collecting assembly that collects radiation reflected from the surface, wherein the reflected radiation collecting assembly comprises a mirror to collect radiation reflected from the surface.

16 Claims, 6 Drawing Sheets

U.S. PATENT DOCUMENTS

| | | |
|---|---|---|
| 6,757,056 B1 | 6/2004 | Meeks et al. |
| 6,781,103 B1 | 8/2004 | Lane |
| 7,002,675 B1 * | 2/2006 | MacGibbon et al. ..... 356/237.2 |
| 2002/0015146 A1 | 2/2002 | Meeks |
| 2002/0145740 A1 | 10/2002 | Meeks |
| 2002/0163634 A1 | 11/2002 | Meeks |
| 2003/0025905 A1 | 2/2003 | Meeks |
| 2004/0017561 A1 | 1/2004 | Meeks |
| 2004/0046959 A1 | 3/2004 | Meeks |
| 2004/0125369 A1 * | 7/2004 | Wang ..................... 356/237.2 |
| 2004/0160604 A1 | 8/2004 | Meeks |
| 2004/0169850 A1 | 9/2004 | Meeks |
| 2004/0233419 A1 | 11/2004 | Meeks |
| 2005/0023491 A1 * | 2/2005 | Young et al. .......... 250/559.42 |
| 2005/0057747 A1 | 3/2005 | Meeks |

* cited by examiner

WAFER EDGE INSPECTION

RELATED APPLICATIONS

This application is a continuation-in-part of U.S. patent application Ser. No. 11/123,913, filed May 6, 2005, entitled Wafer Edge Inspection, the disclosure of which is incorporated herein by reference.

BACKGROUND

The subject matter described herein relates to surface inspection techniques, and more particularly to wafer edge inspection.

Semiconductor materials may be inspected for defects such as, e.g., surface imperfections, particles, irregularities in the thickness of thin film coatings, and the like, which may hamper the performance of the semiconductor material. Some existing inspection systems direct a beam of radiation on the surface of the semiconductor material, then collect and analyze light reflected and/or scattered from the surface to quantify characteristics of the surface. Additional inspection techniques are desirable. In particular, it is desirable to inspect the edge or near edge of semiconductor wafers, compound semiconductor wafers, transparent wafers or thin film disks for defects such as particles, scratches, pits, mounds, cracks, blisters, missing films, chips, and other defects.

BRIEF DESCRIPTION OF THE DRAWINGS

The detailed description is described with reference to the accompanying figures.

DETAILED DESCRIPTION

Described herein are exemplary systems and methods for wafer edge inspection. In the following description, numerous specific details are set forth in order to provide a thorough understanding of various embodiments. However, it will be understood by those skilled in the art that the various embodiments may be practiced without the specific details. In other instances, well-known methods, procedures, components, and circuits have not been described in detail so as not to obscure the particular embodiments.

Various methods described herein may be embodied as logic instructions on a computer-readable medium. When executed on a processor the logic instructions cause a processor to be programmed as a special-purpose machine that implements the described methods. The processor, when configured by the logic instructions to execute the methods described herein, constitutes structure for performing the described methods.

Figure 1:
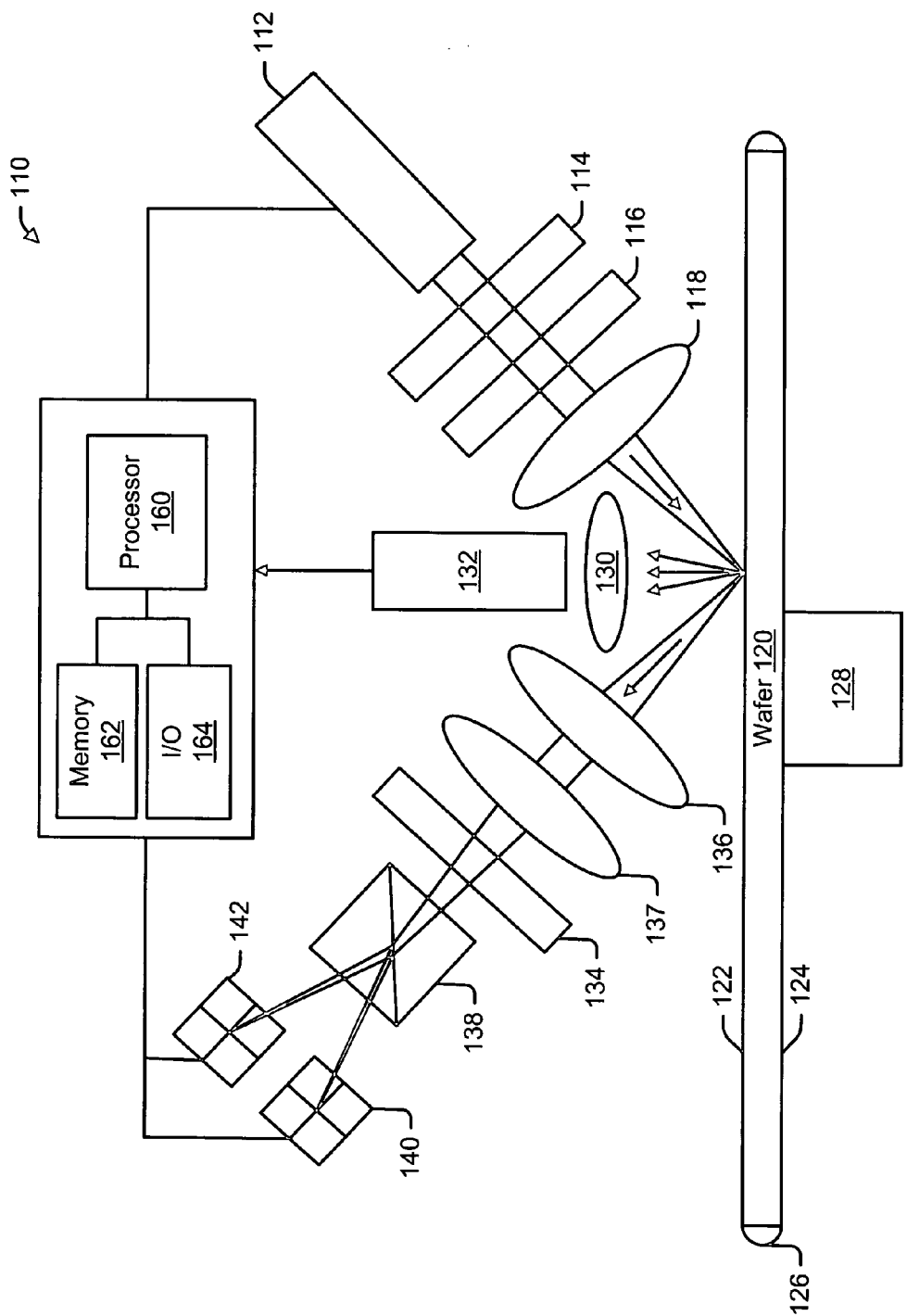
FIG. 1 is a schematic illustration of various optical components of an embodiment of an apparatus for wafer edge inspection.

FIG. 1 is a schematic illustration of one embodiment of an apparatus for wafer or disk edge inspection. Various optical testing components and techniques for surface inspection are described in U.S. Pat. Nos. 6,665,078, 6,717,671, and 6,757,056 to Meeks, et al., the disclosures of which are incorporated herein by reference in their entirety. Any of the assemblies and techniques described in these patents may be used in a surface analyzer for wafer edge inspection.

One embodiment is adapted to perform film thickness measurements, surface roughness measurement, reflectivity measurement, magnetic imaging, and optical profiling using radiation in the optical spectrum. In alternate embodiments radiation outside the optical spectrum may be used. More particularly, FIG. 1 depicts an optics assembly capable of performing that includes a combined reflectometer, scatterometer, phase shift microscope, magneto-optic Kerr effect microscope and optical profilometer. This embodiment is capable of detecting and classifying a wide variety of defects at a wafer or disk edge or near edge.

Wafer 120 includes an upper surface 122, a lower surface 124, and an edge surface 126, which may be substantially flat or curved when viewed in a cross-sectional profile. In the embodiment depicted in FIG. 1, the wafer edge surface is curved when viewed in cross-sectional profile.

A surface analyzer assembly 110 is positioned to direct radiation onto a surface of wafer 120. In the embodiment depicted in FIG. 1, surface analyzer assembly 110 includes a laser diode 112, an optional polarizer 114, an optional half-wave plate 116, and a focusing lens 118 for directing radiation onto a surface of wafer 120. These components target radiation from the laser diode onto the surface of wafer 120, and hence may be considered a radiation targeting assembly. In alternative embodiment polarizer 114 and half-wave plate 116 may be omitted.

Surface analyzer assembly 110 further includes a collecting lens 130 and a photomultiplier tube (PMT) 132. These components collect radiation scattered by the surface of the wafer 120, and hence may be considered a scattered radiation assembly. In alterative embodiments the PMT 132 and collecting lens 130 may be replaced with an integrating sphere or an ellipsoidal mirror together with a PIN photodiode or avalanche photodiode.

Surface analyzer assembly 110 further includes a collimating lens 136, a wobble reduction lens 137, a quarter wave plate 134, a Wollaston prism 138 rotated at 45 degrees to the plane of incidence, and two quadrant detectors 140, 142 available from Hamamatsu, Inc. In another embodiment, detectors 140 and 142 may be PIN photodetectors also available from Hamamatsu, Inc. The embodiment shown in FIG. 1 utilizes quadrant detectors so that the slope of the surface may be measured. The surface slope may be integrated to produce the surface profile. These components collect radiation reflected from the surface of wafer 120, and hence may be considered a reflected radiation assembly. The wobble reduction lens 137 is a converging lens. In alternative embodiments the wobble reduction lens 137 and the collimating lens 136 may be combined into a single lens. The wobble reduction lens is chosen so that its focal length is substantially equal to the distance between wobble reduction lens 137 and the quadrant detectors 140 and 142. When this is done the surface slope measured at the quadrant detectors will be minimized. That is, the system will be most tolerant of wobble of the wafer. Another embodiment would position the detectors 140 and 142 at a distance slightly longer or shorter than the focal length of the wobble reduction lens 137. In this case the system would have some sensitivity to both wafer wobble and to surface slope.

In one embodiment surface analyzer assembly 110 uses a multi-mode, multi-wavelength laser diode 112 which is available from Rohm Co., LTD Kyoto, Japan as model number RLD-78MV and a polarizer 114 which is adjusted for P polarization and improves the extinction ratio of the laser. The radiation may be of any wavelength. In one embodiment a 405 nm violet source available from Coherent, Inc may be implemented. In another embodiment a 635 nm source may be implemented. The mechanically rotatable half wave plate 116 is available from CVI Laser Corp. and can be used to rotate the polarization between 45 degrees, and P or S polarization's. Alternative techniques for rotating the polarization include rotating the laser diode 112 or to use a liquid crystal polarization rotator such as model LPR-100 available from Meadowlark Optics, Frederick, Colo. The latter embodiment has the advantage of being a purely electronic means of polarization rotation and as a result there is no possibility of beam movement when the polarization is rotated.

Focusing lens 118 creates a small spot on the surface of a wafer 120. The PMT 132 and collecting lens 130 are used to measure the scattered light for the purposes of computing the surface roughness, measuring debris, detecting stains, cracks, scratches, delaminations, blisters or corrosion on the disk or wafer 120 surface or edge 126 or near edge regions.

After reflecting from the disk, the beam passes through the collimating lens 136, the wobble reduction lens 137, and a quarter-wave plate 134. The beam is then polarization split with a Wollaston prism 138 available from CVI Laser Corp., for example, and each polarization component is detected with separate photodetectors 140, 142. The plane of the Wollaston prism (the plane of the S and P components) may be adjusted at substantially 45 degrees to the plane of incidence. The first mixed component of the beam (which includes both P and S components with respect to the plane of incidence) is directed to a detector 140 and the second mixed component (which includes both P and S components with respect to the plane of incidence) is directed to a second detector 142. In one embodiment the photodetectors 140, 142 may have a diffuser placed in front of them to reduce the residual position sensitivity of the photodiodes. The difference between the intensity measured by the photodetectors is proportional to the cosine of the phase difference between the first and second mixed components coming from the Wollaston prism. As a result this instrument can get different types of information when used in different modes.

When the polarization is adjusted to P, the P specular and P scattered light is measured resulting in sensitive measurements of carbon thickness (or any simple layer thickness) and carbon wear. The P specular signal is obtained by rotating the half wave plate 116 so that the polarization output from the half wave plate is P polarized. The P specular signal is given by the sum of the signal from 140 and 142. When the polarization is adjusted to 45 degrees (exactly between P and S polarization) the instrument is most sensitive to measurements of the phase change induced by changes in the thickness of the thin films on the disk or wafer surface. In the phase shift mode the instrument measures lubricant, carbon, or other film thickness changes on thin film disks or wafers. The phase shift is measured by taking the difference between the signals measured at 142 and 140. This gives an output that is proportional to the cosine of the phase difference between the first and second mixed components of the wave. The orientation of the quarter wave plate 134 is adjusted to optimize the sensitivity to lubricant, carbon wear, other film thickness changes or changes in phase due to the presence of defects. The individual components may also be measured; that is, the first and second mixed components of the 45 degrees polarized light. These are measured simultaneously with the phase shift and the scattered light.

When the half wave plate is rotated so that the polarization is adjusted to S polarization the instrument will be able to measure the S specular and the S scattered light and, as a result, obtain the surface roughness and other properties of the sample. The S specular signal is given by the sum of the signal from 140 and 142. The angle of incidence shown in FIG. 1 is 58 degrees but angles greater or less than 58 degrees will work as well. The longitudinal Kerr effect can be measured by operating the instrument in any of the linear polarization's, i.e., P, S or 45 degrees. Rotating the quarter wave plate 134 to achieve maximum sensitivity to the magnetic pattern optimizes the Kerr effect signal. The orientation of the quarter wave plate which optimizes the Kerr effect may be different from that which optimizes for lubricant and carbon sensitivity. As a result the quarter wave plate is made to be removable, for example, so that two different and separately optimized plates can be used for the different applications. A different embodiment would have a miniature motor to rotate the orientation of the quarter wave plate so as to optimize the signal for the Kerr effect, lubricant, carbon or defect detection mode. Different polarizations may require a different quarter wave plate adjustment to achieve optimization. When in this mode the instrument functions as a Kerr effect microscope. In one embodiment the S polarization is used to image the longitudinal Kerr effect. When the surface is imaged by the OSA in S linear polarization the reflected light has its polarization converted to elliptical polarization whose major axis is rotated depending upon the orientation of the magnetization upon the thin film disk. This Kerr effect signal is detected by measuring the two signals coming from the polarization beam splitter and subtracting them. This will give a signal whose sign is related to the direction of the magnetization and whose amplitude is proportion to the magnetization.

The data collected by the scattered radiation collection assembly and the reflected radiation collection assembly is fed to a processing module that includes a processor 160, a memory module 162, and an I/O module 164. Processor module comprises logic instructions that enable the instrument described in FIG. 1 to simultaneously measure the profile (height and depth) of the surface, the S and P components of the reflectivity, the phase shift between the P and S waves and the scattered light. It is also capable of measuring the Magneto-optic Kerr effect.

The measurement of the phase shift between the S and P components of the optical wave requires a means to stabilize the long-term phase drift of the diode laser. This can be accomplished by the use of a reference mirror. The reference mirror is a stable surface such as a gold mirror, a section of a thin film disk, or section of a silicon wafer. The reference mirror is calibrated when the instrument is first set up by measuring and recording the phase shift of the reference mirror. At times after the initial calibration of the instrument the reference mirror is measured prior to a measurement of the sample. Any deviation of the reference mirror reading from the initial reading is recorded and subtracted from the measurement of the sample readings. This insures that the phase shift reading from the surface under measurement will remain stable over time. The same procedure can also be applied to the measurement of the S specular and P specular signals. In this case when the instrument is calibrated the values of the P specular and S specular signals measured on the reference mirror are recorded and deviations from these values are used to correct the specular data. This removes any drift from the P and S specular signals.

The above discussion is relating to an instrument, which has an angle of incidence that is near 60 degrees from the vertical. Similar ideas can be applied to a machine operating at angles less than or greater than 60 degrees. When the angle of incidence changes the interpretation of the various quadrants of the histogram will change.

Figure 2:
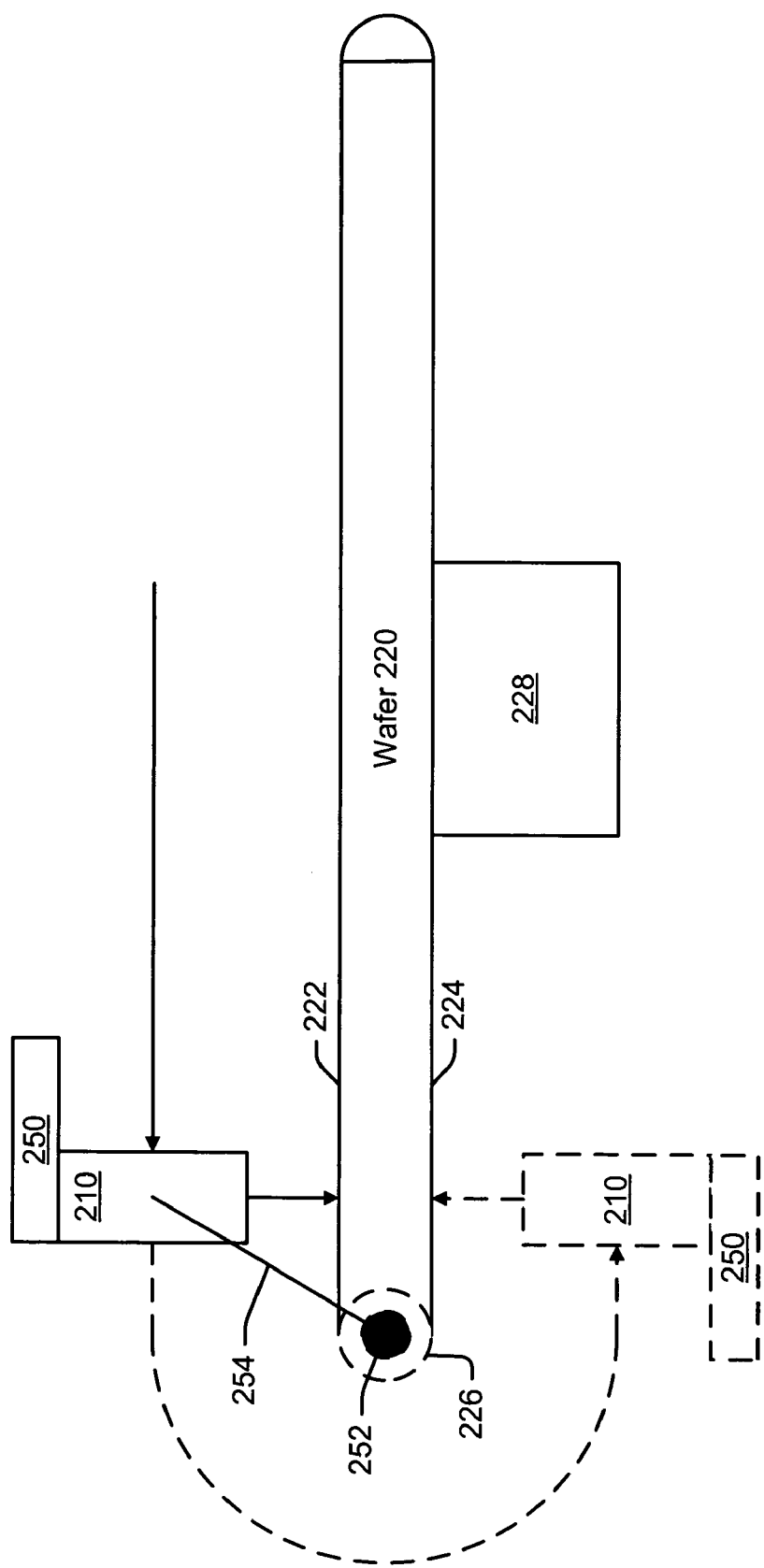
FIG. 2 is a schematic illustration of one embodiment of an apparatus for wafer edge inspection.

FIG. 2 is a schematic illustration of one embodiment of an apparatus for wafer edge inspection. During the inspection process a wafer 220 may be rotated about a central axis on a spindle 228, which may be connected to a suitable motor or other drive assembly for inducing rotational motion to the spindle. A first drive assembly including, e.g., a motor for moving the head in the horizontal direction 250 moves a surface analyzer assembly 210 as described herein or as described in U.S. Pat. Nos. 6,665,078, 6,717,671 and 6,757,056 over the wafer surface, generating data about various characteristics of the surface. A second drive assembly including, e.g., a rotational motor connected to the surface analyzer assembly 210 by a suitable linkage 254 provides rotational motion to move the surface analyzer assembly 210 around the edge surface 226 of the wafer in a path illustrated by the dashed arrow in FIG. 2.

In one embodiment the motor producing the linear motion 250 and the rotational motor 252 cooperate to maintain a substantially fixed distance between the surface analyzer assembly 210 and the respective surfaces 222, 224, 226 of the wafer as the surface analyzer assembly 210 rotates about the edge surface 226 of the wafer. The edge of the wafer 226 is not necessarily in the shape of a semicircle but may in general be any type of shape. If motors 250 and 252 are operated in a cooperative manner then the head 210 may be kept at a fixed distance above the wafer edge regardless of the shape of the edge. Optionally, the motor producing the linear motion 250 can cause the surface analyzer assembly 210 to traverse the top 222 and or bottom surface 224 of wafer 220, permitting the surface 224 or 222 to be scanned for defects.

Figure 3:
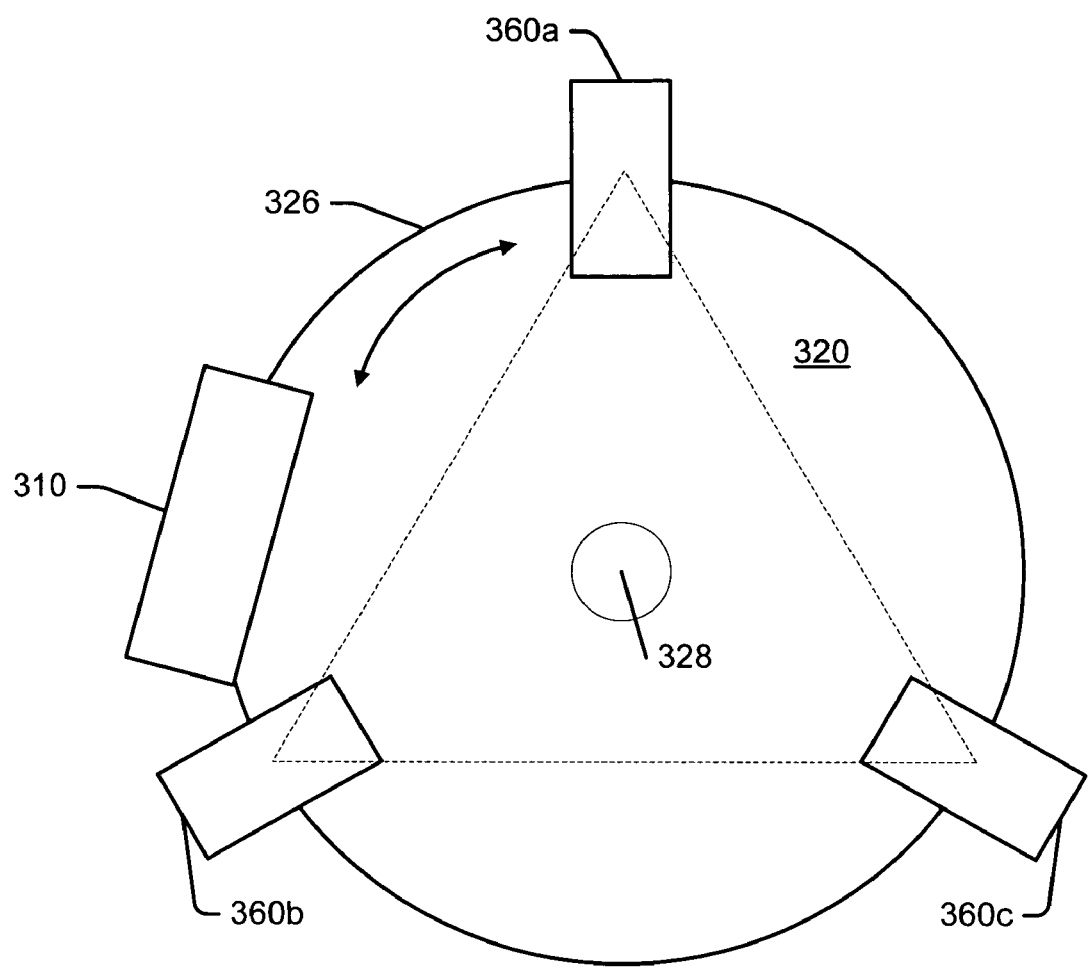
FIG. 3 is a schematic illustration of one embodiment of an apparatus for wafer edge inspection.

In one embodiment the apparatus comprises an assembly for centering the wafer on the spindle, which reduces the lateral variation (or "wobble") in the edge of the wafer as it rotates about a central axis. FIG. 3 is a schematic illustration of a wafer edge inspection system illustrating an assembly for centering the wafer 320. Referring to FIG. 3, a wafer 320 rotates about a central axis on a spindle 328. Wafer 320 may rotate in either direction, as illustrated by the dual-headed arrow. An surface analyzer assembly 310 scans the edge 326 of wafer 320, as described above.

Three positioning heads 360a, 360b, 360c are positioned adjacent three points on the outer edge 326 of wafer 320. In one embodiment the three positioning heads 360a, 360b, 360c are positioned at the respective vertices of an equilateral triangle circumscribed by the edge of wafer 320. However, the positioning heads 360a, 360b, 360c may be otherwise positioned.

The center of the triangle represented by positioning heads 360a, 360b, 360c corresponds to the center of the spindle 328. In one embodiment, the positioning heads 360a, 360b, 360c may be configured to transfer their (x, y) coordinates to the processing module (see, FIG. 1), which calculates the (x, y) coordinates of the center of the wafer 320. The wafer 320 may then be moved such that the center of the wafer 320 corresponds to the center of the spindle 328.

In one embodiment, one or more of the positioning heads 360a, 360b, 360c includes a pushing mechanism such as, e.g., a servo-mechanical plunger to position the wafer 320 over the center of the spindle.

In one embodiment the positioning heads 360a, 360b, 360c are adapted to communicate their respective (x, y) coordinates to the processor 160, which calculates the (x, y) coordinates of the center of the wafer from the positions of the positioning heads. The processor then determines the amount of movement necessary to position the center of the wafer over the center of the spindle, and transmits instructions to the positioning heads to move the wafer 320. In another embodiment the wafer 320 and the positioning heads 360a, 360b, 360c remain fixed in position and the spindle 328 is moved.

In an alternate embodiment an apparatus for surface analysis may use multiple surface analyzer assemblies rather than rotating a single surface analyzer assembly around multiple surfaces of a wafer. For example, a first surface analyzer assembly may scan an upper surface of the wafer, while a second surface analyzer assembly may scan an edge surface of the wafer and a third surface analyzer may scan a lower surface of the wafer.

Figure 4:
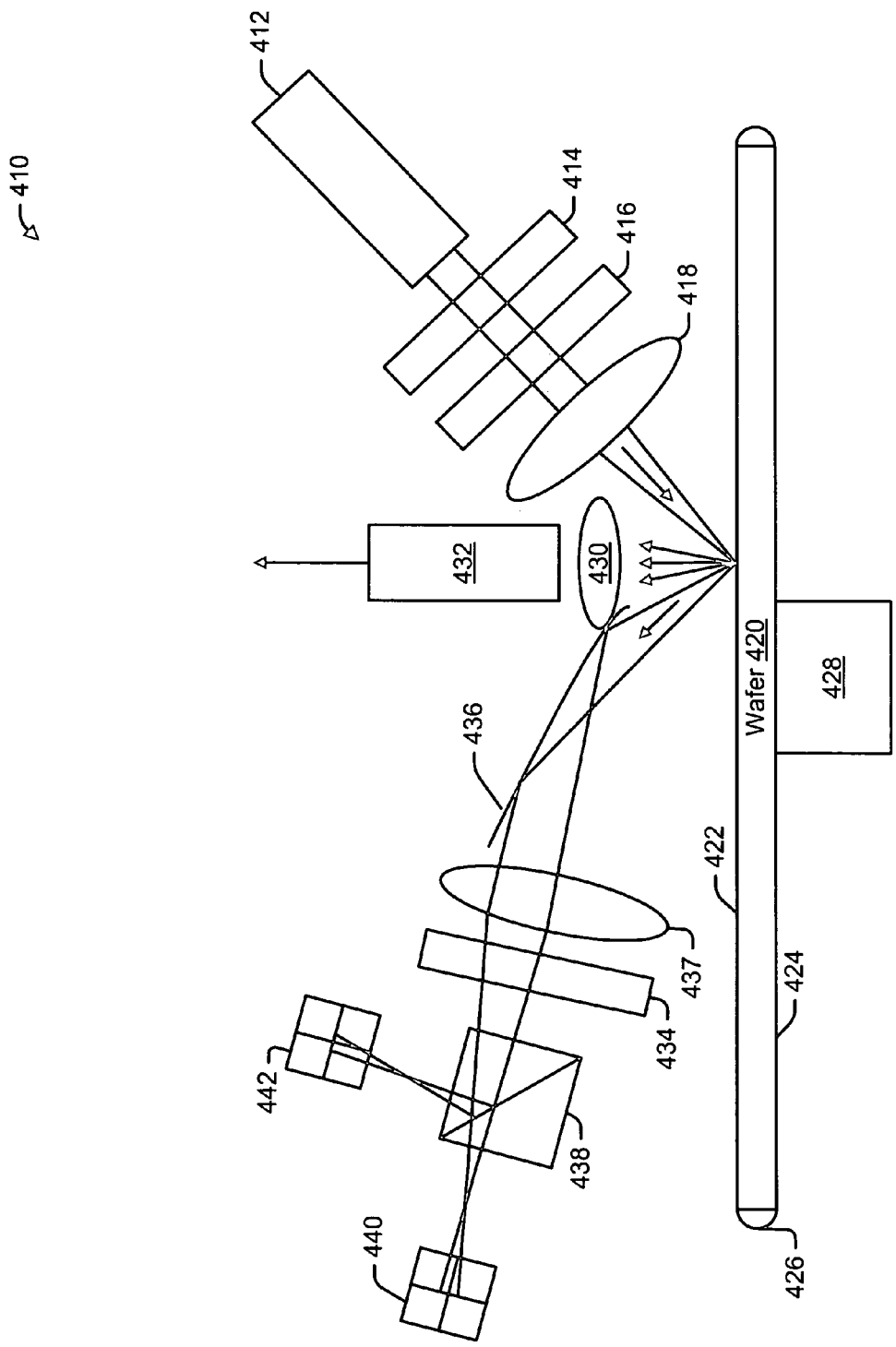
FIG. 4 is a schematic illustration of various optical components of an embodiment of an apparatus for wafer edge inspection.

FIG. 4 is a schematic illustration of various optical components of an embodiment of an apparatus for wafer edge inspection. Wafer 420 includes an upper surface 422, a lower surface 424, and an edge surface 426, which may be substantially flat or curved when viewed in a cross-sectional profile. In the embodiment depicted in FIG. 4, the wafer edge surface is curved when viewed in cross-sectional profile.

A surface analyzer assembly 410 is positioned to direct radiation onto a surface of wafer 420. In the embodiment depicted in FIG. 4, surface analyzer assembly 410 includes a laser diode 412, an optional polarizer 414, an optional half-wave plate 416, and a focusing lens 418 for directing radiation onto a surface of wafer 420. These components target radiation from the laser diode onto the surface of wafer 420, and hence may be considered a radiation targeting assembly. In alternative embodiment polarizer 414 and half-wave plate 416 may be omitted.

Surface analyzer assembly 410 further includes a collecting lens 430 and a photomultiplier tube (PMT) 432. These components collect radiation scattered by the surface of the wafer 420, and hence may be considered a scattered radiation assembly. In alterative embodiments the PMT 432 and collecting lens 430 may be replaced with an integrating sphere or an ellipsoidal mirror together with a PIN photodiode or avalanche photodiode.

Surface analyzer assembly 410 further includes a reflecting mirror 436 to collect light reflected from the surface 422 of wafer 420. In one embodiment, reflecting mirror 436 may be implemented as a paraboloid reflector, e.g., a parabola of revolution. The paraboloid reflector 436 may be positioned such that its focus is approximately coincident with the focus of the laser and the axis of the paraboloid is tilted slightly to allow room for further optical components. Radiation reflected from paraboloid reflector 436 is collimated (i.e., divergence of the light rays is removed).

The collimated beam exiting the paraboloid reflector 436 can move up and down or from side to side (i.e., in and out of the page) due to the shape of the edge. Hence, light collected by the reflecting mirror 436 is directed to a wobble reduction lens 437. The wobble reduction lens 437 directs the collimated beam towards a fixed focus of the lens.

Radiation passing through the wobble reduction lens 437 is directed to a quarter wave plate 434, a polarizing beam splitter 438, and two quadrant detectors 440, 442. The polarizing beam splitter 438 may be a polarizing beam splitter cube, a Wollaston prism or some another suitable polarizing beam splitter. In another embodiment detectors 440, and 442 may be PIN photodetectors also available from Hamamatsu, Inc. These components collect radiation reflected from the surface of wafer 420, and hence may be considered a reflected radiation collection assembly.

In one embodiment, the detectors 440, 442 may be placed at or slightly behind the fixed focus of the wobble reduction lens 437. If the detectors are placed slightly behind or in front of the fixed focus of the anti-wobble lens, then a profile (topography) signal may be detected with the quad detectors. In this manner the slope of the edge of the wafer may be measured. The profile of the edge may be determined by integrating the slope of the edge.

In one embodiment, scattered light may be collected by removing a portion part of the reflecting mirror 436 to the right of the focus and placing a PMT 432 (or avalanche photodiode or PIN photodiode) above this location. Optionally, a collecting lens 430 may be included.

Detectors 440, 442 and PMT 432 may have outputs connected to a processing module substantially as described in FIG. 1 to process the output substantially as described above.

Figure 5:
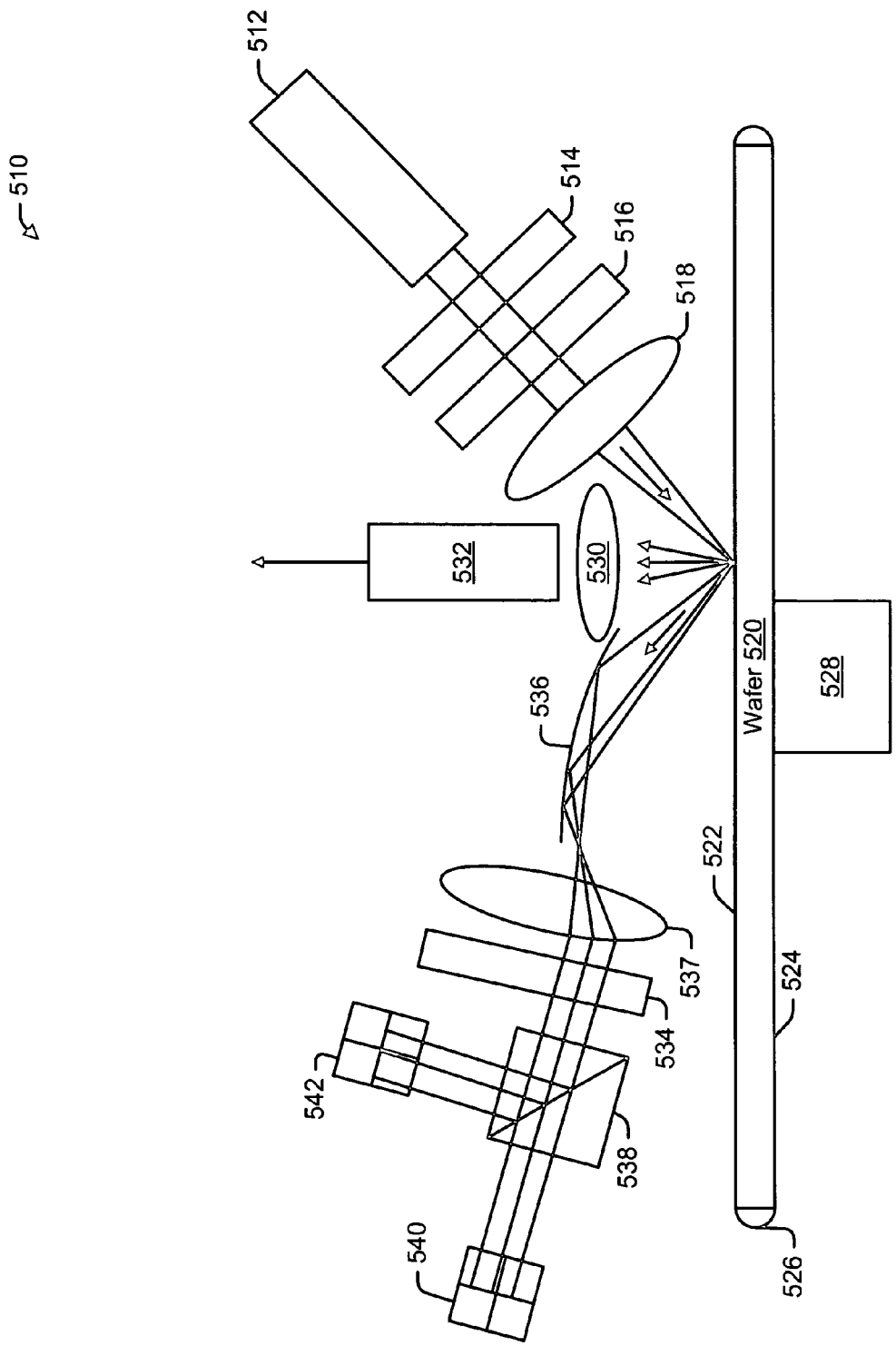
FIG. 5 is a schematic illustration of various optical components of an embodiment of an apparatus for wafer edge inspection.

FIG. 5 is a schematic illustration of various optical components of in an alternate embodiment of an apparatus for wafer edge inspection. A surface analyzer assembly 510 is positioned to direct radiation onto a surface of wafer 520. In the embodiment depicted in FIG. 5, surface analyzer assembly 510 includes a laser diode 512, an optional polarizer 514, an optional half-wave plate 516, and a focusing lens 518 for directing radiation onto a surface of wafer 520. These components target radiation from the laser diode onto the surface of wafer 520, and hence may be considered a radiation targeting assembly. In alternative embodiment polarizer 514 and half-wave plate 516 may be omitted.

Surface analyzer assembly 510 further includes a collecting lens 530 and a photomultiplier tube (PMT) 532. These components collect radiation scattered by the surface of the wafer 520, and hence may be considered a scattered radiation assembly. In alterative embodiments the PMT 532 and collecting lens 530 may be replaced with an integrating sphere or an ellipsoidal mirror together with a PIN photodiode or avalanche photodiode.

Surface analyzer assembly 510 further includes a reflecting mirror 536 to collect light reflected from the surfaces 522, 526, or 524 of wafer 520. In on embodiment, reflecting mirror 536 may be implemented as an ellipsoidal (that is, an ellipse of revolution) reflector. The ellipsoidal reflector 536 may be positioned such that its first focus is approximately coincident with the focus of the laser and the axis of the ellipsoid is tilted slightly to allow room for further optical components. Radiation reflected from the ellipsoidal reflector 536 is directed to its second focal point between the reflector 536 and a collimating lens 537. The collimating lens 537 is placed one focal length from the second focus of the ellipsoidal mirror 536. In this manner the light exiting the collimating 537 lens will be collimated.

The collimated beam exiting the collimating lens 537 is directed to a quarter wave plate 534, a polarizing beam splitter 538, and two quadrant detectors 540, 542. The polarizing beam splitter 538 may be a polarizing beam splitter cube, a Wollaston prism or some another suitable polarizing beam splitter. In another embodiment detectors 540, and 542 may be PIN photodetectors also available from Hamamatsu, Inc. These components collect radiation reflected from the surface of wafer 520, and hence may be considered a reflected radiation collection assembly.

Detectors 540, 542 and PMT 532 may have outputs connected to a processing module substantially as described in FIG. 1 to process the output substantially as described above.

Figure 6:
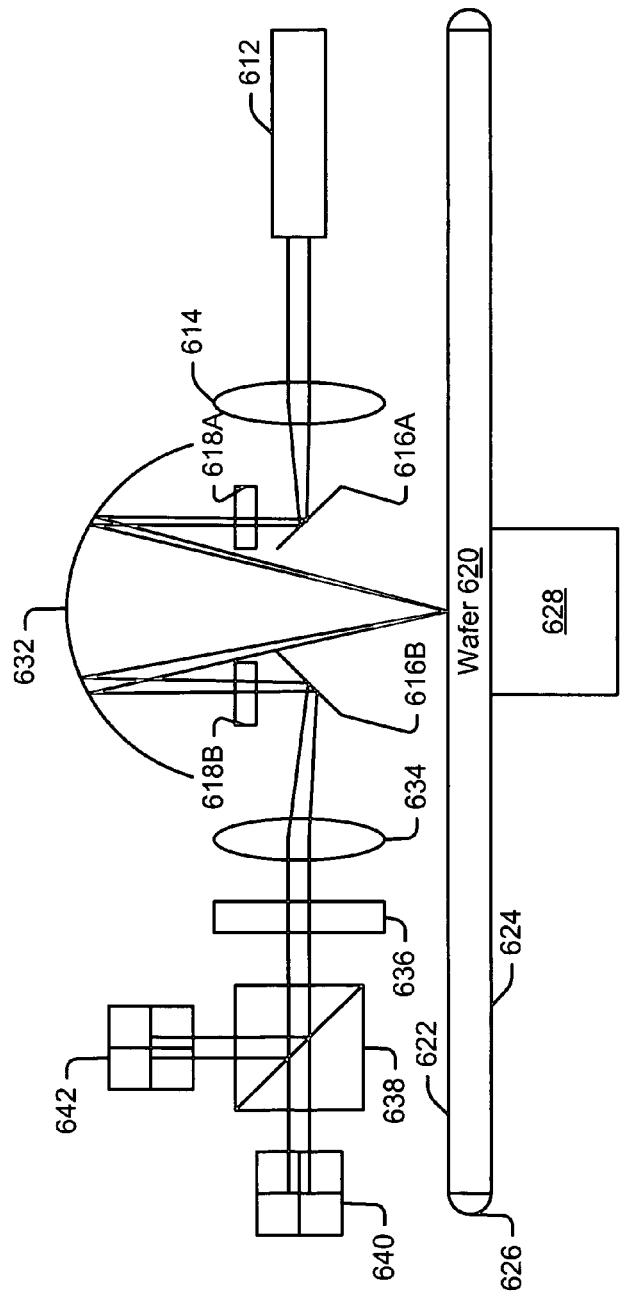
FIG. 6 is a schematic illustration of various optical components of an embodiment of an apparatus for wafer edge inspection.

FIG. 6 is a schematic illustration of various optical components of an embodiment of an apparatus for wafer edge inspection. Wafer 620 includes an upper surface 622, a lower surface 624, and an edge surface 626, which may be substantially flat or curved when viewed in a cross-sectional profile. In the embodiment depicted in FIG. 6, the wafer edge surface is curved when viewed in cross-sectional profile.

A surface analyzer assembly 610 is positioned to direct radiation onto a surface of wafer 620. In the embodiment depicted in FIG. 6, surface analyzer assembly 610 includes a laser diode 612 and a focusing lens 614 for directing radiation onto a surface of turning mirror 616A. Mirror 616A reflects light onto the surface of a spherical or hemispherical mirror 632. In one embodiment the radiation reflected from mirror 616A may pass through a Schmidt corrector plate 618A.

Radiation reflected from spherical mirror 632 is reflected onto the surface 622, and a portion of the radiation incident on surface 622 is reflected back to spherical mirror 632, which reflects the radiation onto turning mirror 616B. In one embodiment the radiation reflected from spherical mirror 632 onto mirror 616B may pass through a Schmidt corrector plate 618B.

Radiation reflected from turning mirror 616B passes through collimating lens 634, quarter-wave plate 636, and onto polarizing beam splitter 638 (which is rotated at 45 degrees to the plane of incidence), which directs the split beams onto detectors 640, 642. The polarizing beam splitter 638 may be a polarizing beam splitter cube, a Wollaston prism or some another suitable polarizing beam splitter. In another embodiment detectors 640, and 642 may be PIN photodetectors also available from Hamamatsu, Inc. These components collect radiation reflected from the surface of wafer 620, and hence may be considered a reflected radiation collection assembly.

In one embodiment, scattered light may be collected by removing a portion part of the spherical mirror 632, e.g., in the center of the spherical mirror, and placing a PMT (or avalanche photodiode or PIN photodiode) above this location. Optionally, a collecting lens may be included.

In another embodiment one or more of the edge scanning devices described herein may be combined with another tool for scanning for defects on the flat part of the wafer (top or bottom). Such a combined tool may include the edge scanning device together with an automation device (e.g., a robot) for handling the wafers and a second tool, possibly within the same enclosure, for scanning the flat top or bottom of the wafer for defects. For example an edge inspection device as described herein may be combined with a Viper 2430 macro defect inspection tool. The edge scanner and the Viper 2430 may share a common robot for handling the wafers as well as a common mechanical platform (e.g., housing). In this manner, the edge of the wafer may be inspected as well as the flat part within a single inspection tool which shares a common robot. The edge scanner described above may be combined with any number of other inspection or metrology tools to make a device which scans the entire surface (i.e., top, edge and bottom) for various types of defects. Examples of tools which may be combined with the edge scanner include: SP1, SP2, Viper 2401, Viper 2430, KT 2360, AIT-UV, AIT or any other inspection or metrology tool.

Reference in the specification to "one embodiment" or "an embodiment" means that a particular feature, structure, or characteristic described in connection with the embodiment is included in at least an implementation. The appearances of the phrase "in one embodiment" in various places in the specification may or may not be all referring to the same embodiment.

Thus, although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. A surface analyzer system, comprising:
   a radiation targeting assembly to target a radiation beam onto a surface; and
   a reflected radiation collecting assembly that collects radiation reflected from the surface;
   wherein the reflected radiation collecting assembly comprises a mirror to collect radiation reflected from the surface; and
   a first drive assembly to impart linear motion between the surface analyzer and a first surface; and
   a second drive assembly to impart rotary motion between the surface analyzer and the first surface about an axis parallel to the first surface.

2. The system of claim 1, further comprising a third drive assembly to impart rotary motion about an axis perpendicular to the surface.

3. The system of claim 1, wherein the reflected radiation collecting assembly comprises a curved collecting mirror to collect reflected radiation.

4. The system of claim 3, wherein the collecting mirror is a paraboloid collecting mirror.

5. The system of claim 3, wherein the collecting mirror is an ellipsoidal collecting mirror.

6. The system of claim 1, wherein the reflected radiation collecting assembly comprises a spherical mirror.

7. The system of claim 1, further comprising a scattered radiation collecting assembly that collects radiation scattered from the surface.

8. The system of claim 1, further comprising an analysis module that analyzes data generated by radiation scattered from the surface and data generated by radiation reflected from the surface.

9. The system of claim 8, wherein the analysis module includes at least one of a reflectometer, a scatterometer, a phase shift microscope, a magneto-optical Kerr effect microscope, an optical profilometer, or an ellipsometer.

10. A system to inspect an edge of a wafer, comprising:
    a surface analyzer assembly comprising:
       a radiation targeting assembly that targets a radiation beam onto a surface of the wafer;
       a reflected radiation collection assembly that includes a mirror to collect radiation reflected from a surface of the wafer; and
    means for rotating the surface analyzer assembly about an edge surface of the wafer, wherein the mirror is a parabolic mirror or an ellipsoid mirror.

11. The system of claim 10, wherein the reflected radiation collection assembly comprises a spherical mirror with a Schmidt corrector plate.

12. The system of claim 10, further comprising three measuring devices and pushers, wherein the measuring devices locate the central axis of the wafer and align the central axis of the wafer with the central axis of the spindle.

13. The system of claim 10, further comprising an analysis module that analyzes data generated by radiation scattered from a surface of the wafer and data generated by radiation reflected from a surface of the wafer.

14. A surface analyzer system, comprising:
    a radiation source;
    a radiation detector; and
    a spherical mirror to direct radiation from the radiation source onto a surface and to direct radiation reflected from the surface toward the radiation detector; and
    a first radiation targeting assembly to direct radiation from the radiation source to the spherical mirror, the radiation assembly comprising:
       a focusing lens;
       a mirror; and
       a Schmidt corrector plate.

15. The system of claim 14, further comprising a second radiation directing assembly to direct radiation from the surface to the radiation detector, the second radiation assembly comprising:
    a Schmidt corrector plate;
    a collimating lens;
    a quarter wave plate; and
    a beam splitter.

16. The system of claim 14, wherein the analysis module includes at least one of a reflectometer, a scatterometer, a phase shift microscope, a magneto-optical Kerr effect microscope, an optical profilometer, or an ellipsometer.

* * * * *